United States Patent
Etzkorn et al.

(10) Patent No.: US 9,298,020 B1
(45) Date of Patent: Mar. 29, 2016

(54) INPUT SYSTEM

(75) Inventors: James Etzkorn, Mountain View, CA (US); Nathan Pletcher, Mountain View, CA (US); Babak Amirparviz, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 629 days.

(21) Appl. No.: 13/559,288

(22) Filed: Jul. 26, 2012

(51) Int. Cl.
*G02C 1/00* (2006.01)
*G02C 7/04* (2006.01)
*G02C 11/00* (2006.01)

(52) U.S. Cl.
CPC . *G02C 7/04* (2013.01); *G02C 11/10* (2013.01)

(58) Field of Classification Search
CPC .................................. G02C 7/04; G02C 11/10
USPC ................. 351/158, 159.01, 159.02
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |
| 4,555,372 A | 11/1985 | Kunzler et al. | |
| 4,604,479 A | 8/1986 | Ellis | |
| 4,632,844 A | 12/1986 | Yanagihara et al. | |
| 4,686,267 A | 8/1987 | Ellis et al. | |

(Continued)

FOREIGN PATENT DOCUMENTS

| | | |
|---|---|---|
| EP | 0369942 | 5/1990 |
| EP | 686372 | 12/1995 |

(Continued)

OTHER PUBLICATIONS

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

(Continued)

*Primary Examiner* — Huy K Mai
(74) *Attorney, Agent, or Firm* — McDonnell Boehnen Hulbert & Berghoff LLP

(57) ABSTRACT

Apparatus, systems and methods facilitating contact lenses that detect fatigue or emotional state of a wearer of the contact lenses are provided. In some aspects, a contact lens includes: a substrate; one or more sensors disposed on or within the substrate, wherein the one or more sensors senses fatigue and/or an emotional state of a wearer of the contact lens; and an antenna disposed on or within the substrate, that communicates information sensed by the one or more sensors. In various aspects, systems can include the contact lens, a reader that can process the information sensed and an alarm generation component that can generate an alarm based on the determined fatigue and/or emotional state of the wearer of the contact lens.

20 Claims, 10 Drawing Sheets

(56) References Cited

U.S. PATENT DOCUMENTS

| | | |
|---|---|---|
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0058660 A1* | 3/2009 | Torch .................. 340/573.1 |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0103368 A1* | 4/2010 | Amirparviz et al. .......... 351/158 |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |
| 2012/0201755 A1 | 8/2012 | Rozakis et al. |

(56) References Cited

U.S. PATENT DOCUMENTS

| | | |
|---|---|---|
| 2012/0245444 A1 | 9/2012 | Otis et al. |
| 2012/0259188 A1 | 10/2012 | Besling |
| 2013/0258287 A1* | 10/2013 | Pugh et al. ............... 351/210 |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |
| EP | 2457122 | 5/2012 |
| WO | 95/04609 | 2/1995 |
| WO | 0116641 | 3/2001 |
| WO | 01/34312 | 5/2001 |
| WO | 03065876 | 8/2003 |
| WO | 2004/060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010/133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Bionic contact lens 'to project emails before eyes,' http://www.kurzweilai.net/forums/topic/bionic-contact-lens-to-project-emails-before-eyes, Last accessed Mar. 14, 2012, 2 pages.
Tweedie, et al., "Contact creep compliance of viscoelastic materials via nanoindentation," J. Mater. Res., Jun. 2006, vol. 21, No. 2, pp. 1576-1589, Materials Research Society.
Brahim, et al., "Polypyrrole-hydrogel composites for the construction of clinically important biosensors," 2002, Biosensors & Bioelectronics, vol. 17, pp. 53-59.
Huang, et al., "Wrinkling of Ultrathin Polymer Films," Mater. Res. Soc. Symp. Proc., 2006, vol. 924, 6 pages, Materials Research Society.
Zarbin, et al., "Nanotechnology in ophthalmology," Can J Ophthalmol, 2010, vol. 45, No. 5, pp. 457-476.
Selner, et al., "Novel Contact Lens Electrode Array for Multi-electrode Electroretinography (meERG)," IEEE, 2011, 2 pages.
Liao, et al., "A 3-μW CMOS Glucose Sensor for Wireless Contact-Lens Tear Glucose Monitoring," IEEE Journal of Solid-State Circuits, Jan. 2012, vol. 47, No. 1, pp. 335-344.
Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.
Thomas, et al., "Functional Contact Lenses for Remote Health Monitoring in Developing Countries," IEEE Global Humanitarian Technology Conference, 2011, pp. 212-217, IEEE Computer Society.
Pandey, et al., "A Fully Integrated RF-Powered Contact Lens With a Single Element Display," IEEE Transactions on Biomedical Circuits and Systems, Dec. 2010, vol. 4, No. 6, pages.
Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
Liao, et al., "A 3μW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Baxter, "Capacitive Sensors," 2000, 17 pages.
Lingley, et al., "A Single-Pixel Wireless Contact Lens Display," Journal of Micromechanics and Microengineering, 2011, 9 pages.
Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
"Contact Lenses: Look Into My Eyes," The Economist, Jun. 2, 2011, http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Ho et al., "Contact Lens With Integrated Inorganic Semiconductor Devices," MEMS 2008. IEEE 21st International Conference on. IEEE, 2008., pp. 403-406.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Murdan, "Electro-responsive drug delivery from hydrogels," Journal of Controlled Release, 2003, pp. 1-17, vol. 92.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Singh, et al., "Novel Approaches in Formulation and Drug Delivery using Contact Lenses," Journal of Basic and Clinical Pharmacy, May 2011, pp. 87-101, vol. 2, Issue 2.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.

(56) References Cited

OTHER PUBLICATIONS

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Liu, et al., "Miniature Amperometric Self-Powered Continuous Glucose Sensor with Linear Response," Analytical Chemistry, 2012, 7 pages.

* cited by examiner

INPUT SYSTEM

TECHNICAL FIELD

This disclosure generally relates to contact lenses that facilitate detection of fatigue and/or emotional states of wearers of the contact lenses.

BACKGROUND

There are many applications and/or environments in which it is useful to determine fatigue or an emotional state of a person. These environments include, but are not limited to, during operation of a motorized vehicle or aircraft, during operation of machinery, during sleep studies and the like. Accordingly, systems, apparatus and/or methods that facilitate determination of fatigue and/or emotional state of a person are desired.

SUMMARY

In some aspects, a contact lens can include: a substrate; and a circuit. The circuit can include: one or more sensors disposed on or within the substrate, wherein the one or more sensors sense at least one of fatigue or an emotional state of a wearer of the contact lens; and an antenna disposed on or within the substrate, that communicates information sensed by the one or more sensors. In various aspects, alarms can be generated and/or notification of an alarm (or alarm condition) can be transmitted. In some aspects, a signal can be transmitted to cause a particular device being operated by the wearer of the contact lens to perform in a certain manner (e.g., cease operation, fail to commence operation).

In some aspects, a system can include: a contact lens that senses fatigue of a wearer of the contact lens; and a reader that receives a signal from the contact lens, the signal including information indicative of the fatigue of the wearer of the contact lens.

In some aspects, a method can include: sensing, using a contact lens, fatigue of a wearer of the contact lens, wherein the sensing is performed via one or more sensors disposed on or within the contact lens.

DETAILED DESCRIPTION

Figure 1:
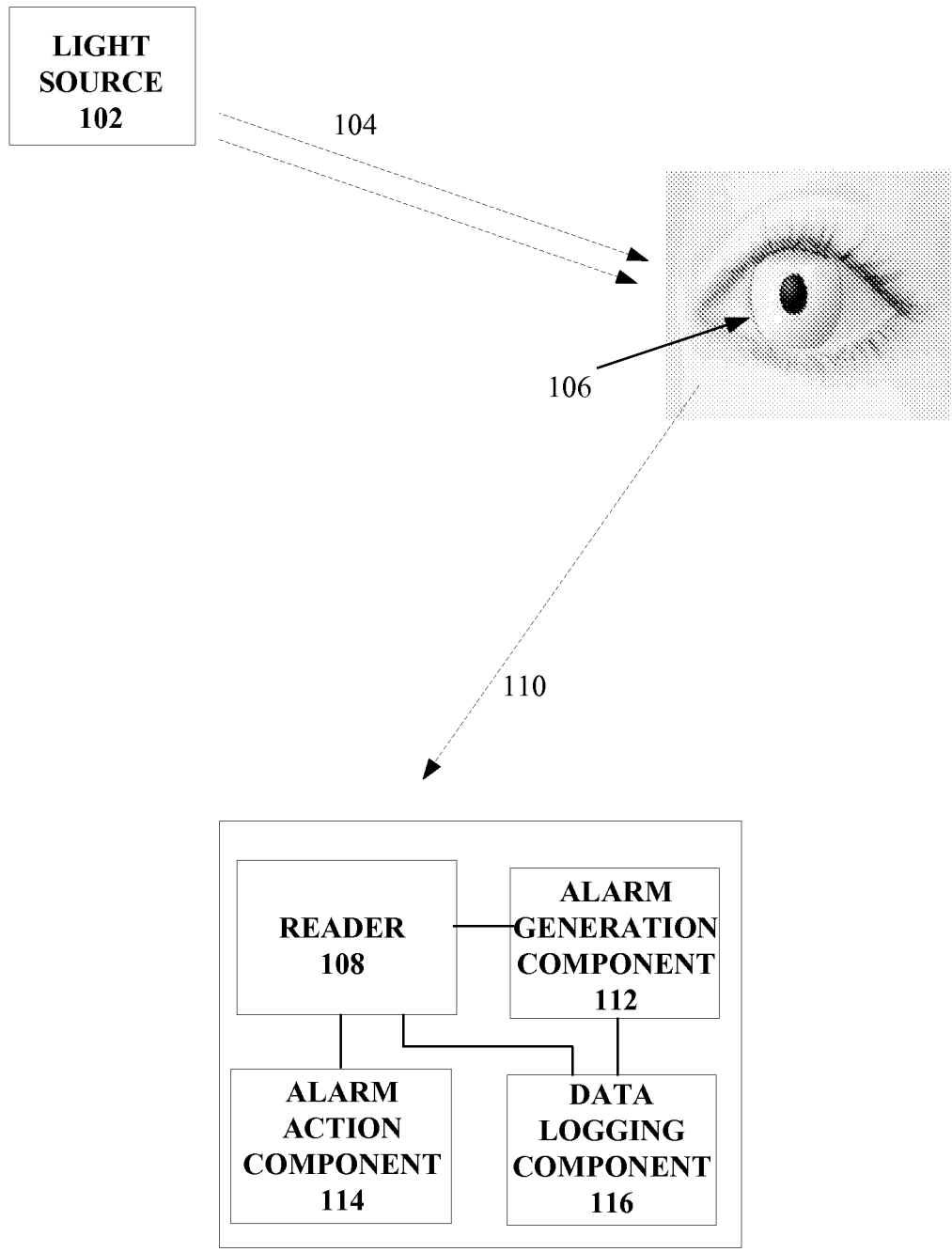
FIG. 1 is an illustration of a block diagram of an exemplary non-limiting system that facilitates detection of fatigue and/or emotional states of wearers of contact lenses.

Various aspects are now described with reference to the drawings, wherein like reference numerals are used to refer to like elements throughout. In the following description, for purposes of explanation, numerous specific details are set forth in order to provide a more thorough understanding of one or more aspects. It is be evident, however, that such aspects can be practiced without these specific details. In other instances, structures and devices are shown in block diagram form in order to facilitate describing one or more aspects.

As used in this application, the terms "component," "component," "system," and the like are intended to refer to a computer-related entity, either hardware, software, firmware, a combination of hardware and software, software and/or software in execution. For example, a component can be, but is not limited to being, a process running on a processor, a processor, an object, an executable, a thread of execution, a program, and/or a computer. By way of illustration, both an application running on a computing device and/or the computing device can be a component. One or more components can reside within a process and/or thread of execution and a component can be localized on one computer and/or distributed between two or more computers. In addition, these components can execute from various computer-readable storage media having various data structures stored thereon. The components can communicate by way of local and/or remote processes such as in accordance with a signal having one or more data packets (e.g., data from one component interacting with another component in a local system, distributed system, and/or across a network such as the Internet with other systems by way of the signal).

The word "exemplary" is used herein to mean serving as an example, instance, or illustration. For the avoidance of doubt, the subject matter disclosed herein is not limited by such examples. In addition, any aspect or design described in this disclosure as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

It is to be appreciated that in accordance with one or more aspects described in this disclosure, users can opt-in or opt-out of providing personal information, demographic information, location information, proprietary information, sensitive information, or the like in connection with data gathering aspects. Moreover, one or more aspects described herein can provide for anonymizing collected, received, or transmitted data.

Apparatus, systems and/or methods disclosed herein relate to contact lenses that facilitate detection of fatigue and/or emotional state of a wearer of contact lenses. In some aspects, behavior of the eyelids (e.g., blinking, eyes closed, etc.), chemical or biomarkers can also be detected. For example, a contact lens can be configured to detect number of blinks of the eye within a predetermined duration of time. If the number of blinks exceeds a particular threshold, the contact lens can determine that the wearer of the contact lens is fatigued.

As another example, the contact lens can be configured to detect light. If no light is detected for a predetermined amount of time, the contact lens can determine that the wearer of the contact lens is asleep.

As another example, the contact lens can be configured to detect level of fluid retention around the eyes. If the level of fluid retention is above a predetermined threshold, the contact lens can determine that the wearer has puffy eyes and is fatigued.

As another example, the contact lens can detect chemical level (e.g., level of serotonin, dopamine, lactate, hydrogen ions or adrenaline) in the wearer of the contact lens. If the levels of serotonin or dopamine are above a predetermined threshold, the wearer can be determined to have a happy emotional state. If the level of adrenaline is less than a predetermined threshold, the wearer can be determined to be fatigued. If the level of lactate or hydrogen ions in above a predetermined threshold, the wearer can be determined to be fatigued.

In some aspects, a contact lens can include: a substrate; and a circuit. The circuit can include: one or more sensors disposed on or within the substrate, wherein the one or more sensors sense at least one of fatigue or an emotional state of a wearer of the contact lens; and an antenna disposed on or within the substrate, that communicates information sensed by the one or more sensors. In various aspects, alarms can be generated and/or notification of an alarm (or alarm condition) can be transmitted. In some aspects, a signal can be transmitted to cause a particular device being operated by the wearer of the contact lens to perform in a certain manner (e.g., cease operation, fail to commence operation).

In some aspects, a system can include: a contact lens that senses fatigue of a wearer of the contact lens; and a reader that receives a signal from the contact lens, the signal including information indicative of the fatigue of the wearer of the contact lens.

In some aspects, a method can include: sensing, using a contact lens, fatigue of a wearer of the contact lens, wherein the sensing is performed via one or more sensors disposed on or within the contact lens.

One or more aspects of the apparatus, systems and/or methods described herein can advantageously facilitate detection of fatigue and/or particular emotional states and, in some aspects, advantageously perform subsequent operations to enhance conduct and/or performance in daily operations. For example, in some aspects, detection of fatigue can lead to a determination (or inference) of whether a driver/pilot/surgeon is falling asleep (or is likely to fall asleep in the near future). In some aspects, the detection of fatigue can lead to a determination (or inference) of duration of different sleep cycles including, but not limited to, duration of rapid eye movement (REM) sleep. Such information can be particularly useful during sleep studies, for example. In some aspects, the emotional state can be monitored by a mental health professional to determine whether adjustment of medication may be desired.

FIG. 1 is an illustration of a block diagram of an exemplary non-limiting system that facilitates detection of fatigue and/or emotional states of wearers of contact lenses. The system 100 can include a light source 102 that emits light rays 104, a contact lens 106 that can facilitate detection of fatigue and/or emotional state of the wearer of the contact lens, a reader 108 that can receive information 110 indicative of the detected fatigue and/or emotional state of the wearer of the contact lens 106, an alarm generation component 112, an alarm action component 114 and/or a data logging component 116. While the system 100 displays light source 102, in some aspects, no light source is included in the system 100. Rather, ambient light is employed to detect fatigue and/or emotional states of wearers of the contact lenses. As such, the system 100 can include the contact lens 106, reader 108, alarm generation component 112, alarm action component 114 and/or data logging component 116. In one or more aspects, one or more of the components of system 100 can be communicatively and/or electrically (or optically) coupled to one another to perform one or more functions of the system 100.

Light 104 can be emitted from light source 102 and be incident on the contact lens 106. The contact lens 106 can include circuitry to determine (or infer) whether the wearer of the contact lens 106 is experiencing fatigue and/or to identify the emotional state of the wearer. In various aspects, the contact lens 106 can determine various eye behavior including, but not limited to, a duration of time during which the eye on which the contact lens 106 is worn is closed, the frequency of blinking of the eyelid, swollen or puffy eyes, level of adrenaline, epinephrine and/or norepinephrine in the body of the wearer of the contact lens 106. Eye behavior can also be employed to determine (or infer) whether the wearer of the contact lens 106 is experiencing fatigue and/or is asleep. For example, the circuit (not shown) of the contact lens 106 can be configured to detect number of blinks of the eye within a predetermined duration of time. If the number of blinks exceeds a particular threshold, the circuit can determine (or infer) that the wearer of the contact lens 106 is fatigued. As another example, the circuit can be configured to detect light. If no light is detected for a predetermined amount of time, the circuit can determine that the wearer of the contact lens 106 is asleep. As another example, the circuit can be configured to detect level of adrenaline, epinephrine and/or norepinephrine in the body of the wearer of the contact lens 106. If the level of adrenaline, epinephrine and/or norepinephrine in the body of the wearer of the contact lens 106 is lower than a predetermined threshold for the respective chemicals, the circuit can determine that the wearer is fatigued.

It is to be appreciated that in an embodiment, calibration can be performed to determine baseline (or reference) points corresponding to a first user state (e.g., not fatigued or in a normal emotional state), and variance from such baseline points can be employed to determine or infer level or user alertness, fatigue, emotional state, etc.

In another embodiment, a model can be developed based on sample data that can be employed for out of the box determination or inference regarding user state. In an aspect, the model can learn based on specific user behavior in order to converge on accurate predictions, determinations, or inference regarding user state. The model can be learned employing explicit and/or implicit training techniques.

The information 110 generated by the contact lens 106 can be transmitted to reader 108. The reader 108 can be a radio frequency (RF) reader that can receive signals from the contact lens 106.

The reader 108 and/or the alarm generation component 112 can determine or infer whether fatigue and/or a particular emotional state exists within the wearer of the contact lens 106. In some aspects, the contact lens 106 can make such determination. For example, in some aspects, the reader 108 can include threshold information that can be compared to level of chemicals (or number of blinks, etc.) output from the contact lens 106. The reader 108 can compare the levels or number of blinks, for example, to the threshold information. In aspects wherein the level of chemicals or number (or frequency) of blinks exceeds the respective threshold, the reader can send a signal to the alarm action component 114 and/or the alarm generation component 112. The alarm generation component 112 can generate an alarm based, at least, upon receiving the signal from the reader 108. The alarm action component 114 can perform one or more actions based, at least, on the receipt of the signal from the reader 108.

It is to be appreciated that in an embodiment artificial intelligence (AI) techniques can employed to perform a utility-based analysis (e.g., based on a probabilistic, statistical, deterministic, or non-deterministic framework) to assess the benefit of taking automated action against the cost of making an incorrect decision regarding such automated action.

As another example, the reader 108 can merely maintain a record of the chemical levels and/or number of blinks output from the contact lens 106. The record can be updated after the information detected at the contact lens 106 is communicated to the reader 108. The alarm action component 114 can monitor the record stored at the reader 108. If the information exceeds a threshold, the alarm generation component 112 can generate the alarm.

Based on a determination (or inference) that the wearer of the contact lens 106 is fatigued, is experiencing a particular emotional state and/or certain eye behavior has transpired, the alarm generation component 112 can generate an alarm. The alarm can be an audio, visual and/or textual alarm in various aspects.

The alarm can be transmitted to the wearer of the contact lens 106, to a supervisor of a wearer of the contact lens 106 and/or to a third-party monitoring agency (e.g., air traffic control). In various aspects, the alarm can be employed to identify individuals (e.g., factory line operator, surgeon, pilot) that may be fatigued and/or experiencing a particular emotional state and can benefit from a break.

Upon generation of the alarm, the alarm action component 114 can generate and/or send a signal to a device operated by the wearer of the contact lens 106. The signal can be adapted to control various aspects of the operation of the device. By way of example, but not limitation, the signal can cause operation of the device to cease (or cease after a selected amount of time after the alarm has been generated). By way of another example, the signal can cause operation of the device to alter in a manner that can facilitate desired conduct for the wearer of the contact lens 106 and/or others with which the wearer may come into contact. For example, the signal can cause the device to: issue a command to the wearer of the contact lens to prepare to cease operation of the device; issue a message that attempts to alert the wearer to the fatigue and/or emotional state of the wearer; and/or pull the device over to the side of a road on which the device may be operating.

The contact lens 106 will be described in greater detail with reference to FIGS. 2 and 3. In various aspects, the structure and/or functionality of contact lens 200 can be or include the structure and/or functionality of contact lens 106 (and vice versa).

Figure 2:
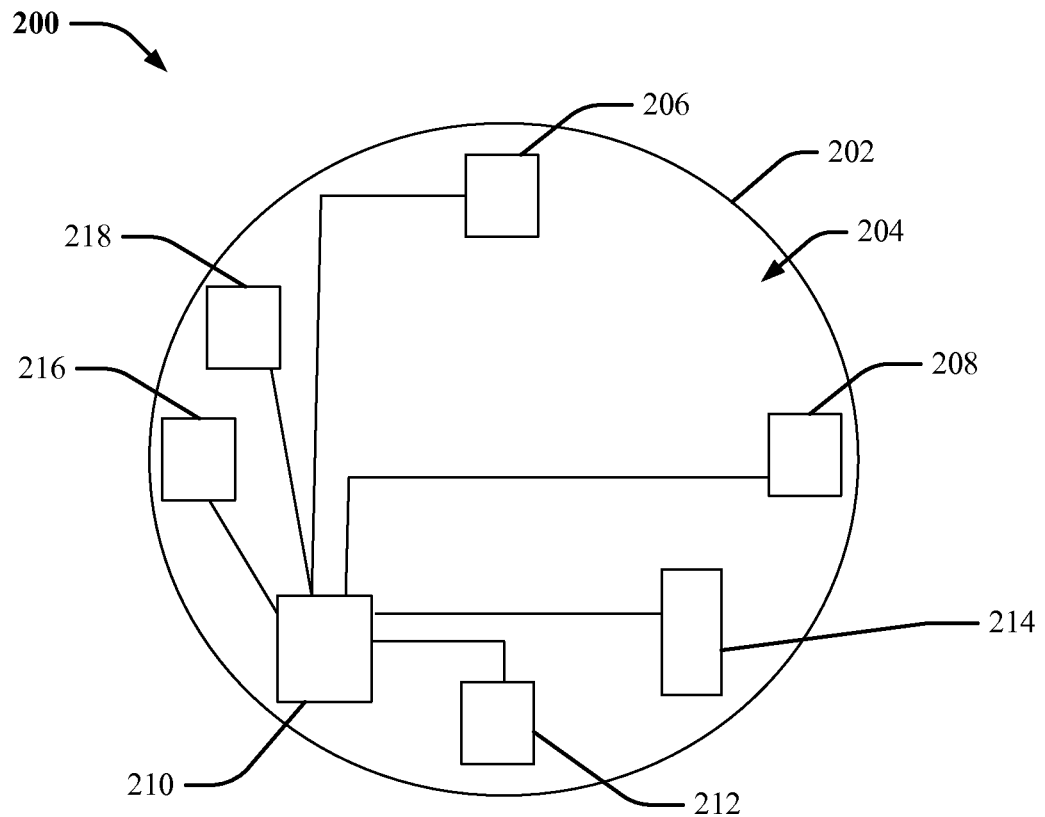
FIG. 2 is an illustration of a block diagram of an exemplary non-limiting contact lens that facilitates detection of fatigue and/or emotional states of wearers of the contact lens.

Turning first to FIG. 2, the contact lens 200 can include a substrate 202 and a circuit 204 that can detect fatigue, emotional states and/or eye behavior of the wearer of the contact lens 200. The circuit can include one or more of the sensors 206, 208, a power component 210, a communication component 212, an analysis component 214, memory 216 and/or microprocessor 218. In various aspects, one or more of the sensors 206, 208, power component 210, communication component 212, analysis component 214, memory 216 and/or microprocessor 218 can be operably, electrically and/or communicatively coupled to one another to perform one or more functions of the circuit 204.

The sensors 206, 208 can be disposed on or within the substrate 202 of the contact lens 200. In various aspects, the sensors 206, 208 can sense information or eye behavior enabling a determination of fatigue or emotional state to be made by the circuit 204.

In various aspects, the sensors 206, 208 can sense whether a wearer of the contact lens 200 is fatigued based on sensing one or more chemicals or biomarkers in the body of the wearer of the contact lens 200. For example, levels of adrenaline, epinephrine, and/or norepinephrine below a particular threshold can be detected and can be determined to indicate fatigue. As another example, level of lactate or hydrogen ions above a particular threshold can be detected and can be determined to indicate fatigue. As another example, a level of fluid near the eye can indicate the level of puffiness of the eye. The level of fluid can be employed to determine (or infer) whether the wearer is fatigued.

In various aspects, the sensors 206, 208 can detect neural and/or electromyogram activity of the wearer of the contact lens 200 to determine whether the wearer of the contact lens 200 is fatigued. For example, the sensors 206, 208 can detect electrical activity from nerve cells in the eye muscles. The electromyogram activity can be the electrical activity from the nerve cells in the eye muscles. If the amount of electrical activity decreases by a predetermined amount over a particular time period, the contact lens 200 can determine that the wearer is fatigued.

In some aspects, the sensors 206, 208 can sense light. As such, the sensors 206, 208 can sense duration of time during which the eye is closed. For example, the duration of time can be the duration of time during which no light is detected at the sensors 206, 208. In some aspects, the duration of time during which the eye is closed can be employed to determine whether a wearer of the contact lens 200 is fatigued or asleep. In an aspect, light detection can also be used to determine frequency of blinking.

In some aspects, the sensors 206, 208 can sense pressure incident on and/or temperature of the contact lens 200 and/or the sensors 206, 208. For example, detection of pressure on and/or temperature on the contact lens 200 and/or sensors 206, 208 can be employed to determine that the eye is closed. By way of example, but not limitation, the pressure can be sensed by a pressure transducer that converts pressure to electricity and/or a MEMS-based device that generates electricity upon a selected amount of pressure (and corresponding stress) being applied to the device. The contact lens 200 can detect the pressure applied to the contact lens 200 based, at least, on the amount of electricity generated on the contact lens 200 in some aspects.

In some aspects, the sensors 206, 208 can sense conductivity within the contact lens. The conductivity can be employed to detect the eye behavior (e.g., blinking). For example, the tissue of the eyelid for the eye over which the contact lens is disposed can have a certain conductivity. The conductivity can increase or decrease based, at least, upon whether the eyelid is open or closed. Accordingly, the conductivity can be a function of the number of times that the eyelid has performed an open and close operation, or a blink operation. The conductivity can be measured and a determination can be made as to whether the conductivity is above a predetermined threshold (for a certain amount of time, e.g., 5 blinks per 20 seconds) that indicates a certain number of blinks. If the conductivity is above the threshold, the contact lens can determine that the wearer is blinking frequently. Blinking frequently can be an indication of fatigue.

As described, in some aspects, a light source can be external to the contact lens 200, and the sensors 206, 208 can sense whether the eye is closed or opened by measuring when the light from the light source is blocked by the eyelid. As such, the sensors 206, 208 can determine whether an eye is open or closed based on this circuitry and/or approach as well. In various aspects, the light source can be ambient light or light from a specified external source.

In various aspects, the sensors 206, 208 can sense the emotional state of the wearer of the contact lens. For example, the emotional state can include, but is not limited to, whether the wearer is happy or sad and/or whether the wearer is experiencing anxiety or a particular stress level. For example, the sensors 206, 208 can sense a level of one or more chemicals (e.g., endorphins, serotonin) in the body of the wearer of the contact lens. If the level is greater than a predetermined value, the emotional state of the wearer can be determined to be happy (or experiencing a stress level that is relatively low). Similarly, if the level is less than a value the emotional state of the wearer can be determined to be sad (or having anxiety).

The analysis component 214 can receive the information sensed by the sensors 206, 208. The analysis component 214 can perform analysis to determine whether particular eye behavior (e.g., blinking) has occurred and/or whether the wearer of the contact lens 200 is fatigued and/or experiencing a particular emotional state.

Figure 3:
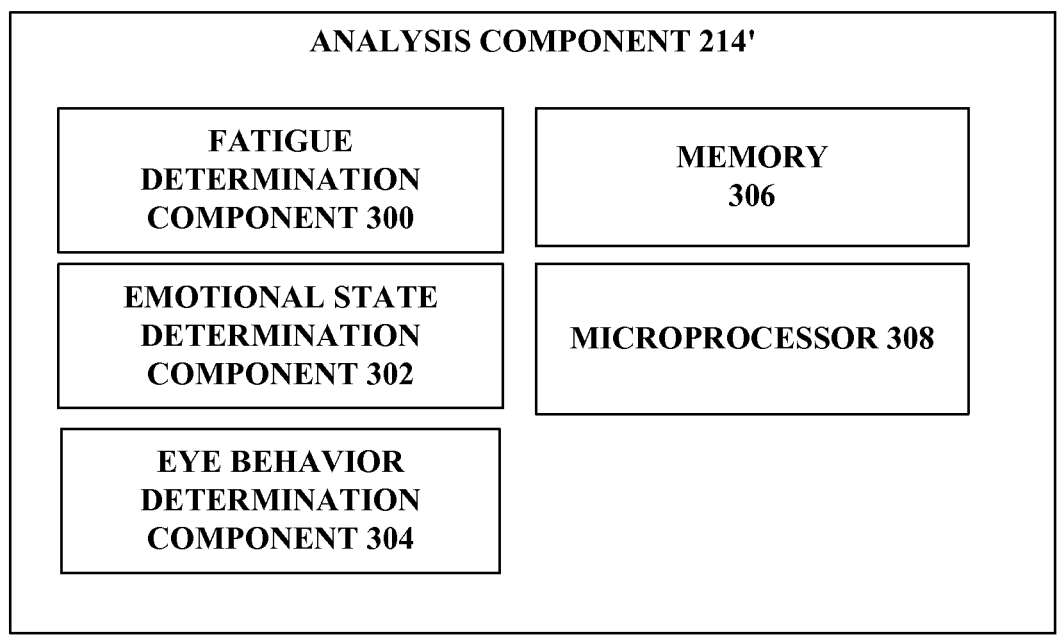
FIG. 3 is an illustration of a block diagram of an exemplary non-limiting system that facilitates detection of fatigue and/or emotional states of wearers of contact lenses.

The analysis component 214 can be described in another aspect such as that shown in FIG. 3. Analysis component 214' can include structure and/or functionality of that described with reference to analysis component 214 (or vice versa). Turning to FIG. 3, in one aspect, the analysis component 214' can include a fatigue determination component 300 that can determine whether the wearer of the contact lens 200 is fatigued, an emotional state determination component 302 that can determine the emotional state of the wearer of the contact lens 200 and/or an eye behavior determination component 304 that can determine behavior (e.g., blinking, eyes closed or open) of the eye of the wearer of the contact lens 200. In some aspects, the analysis component 214' can include a memory 306 and/or a microprocessor 308. In some aspects, the memory 306 and/or microprocessor 308 can be separate from the memory 216 and the microprocessor 218. In other aspects, a single memory and a single microprocessor can be employed on the contact lens 200.

The communication component 212 can communicate with an external reader or other device external to the contact lens 200. In some aspects, the communication component 212 can include an antenna that can communicate with an RF reader. In various aspects, the information communicated by the communication component 212 can be "eye open," "eye closed" and/or information indicative of a biomarker level that can indicate fatigue or an emotional state.

The power component 210 can receive and/or provide power to the sensors 206, 208, communication component 212, analysis component 214, memory 216 and/or microprocessor 218.

In some aspects, the analysis component 214 is not included on the contact lens 200 and the information sensed by the one or more sensors 206, 208 is transmitted to an external reader. The external reader can determine whether particular eye behavior (e.g., blinking) has occurred and/or whether the wearer of the contact lens 200 is fatigued and/or experiencing a particular emotional state.

If fatigue, particular eye behavior and/or a particular emotional state is detected, various actions can be taken including, but not limited to, sending a signal to cause a vehicle being operated by the wearer of the contact lens 200 to pull the vehicle off to the side of the road, alerting or removing an operator (e.g., surgeon, surgical resident, pilot, truck driver, bus driver, factory line employee) from duties.

The memory 216 can be a computer-readable storage medium storing computer-executable instructions and/or information for performing the functions described in this disclosure with reference to the contact lens 200 (or components thereof). The microprocessor 218 can perform one or more of the functions described in this disclosure with reference to the contact lens 200 (or components thereof).

Although one configuration of components is shown for the circuit 204. In other aspects, the circuit 204 can be in any number of other different types of configurations. Further, while the description of FIG. 2 describes two sensors 206, 208, in other aspects, the circuit 204 can include one or more sensors to detect fatigue, emotional states and/or eye behavior.

Figure 4:
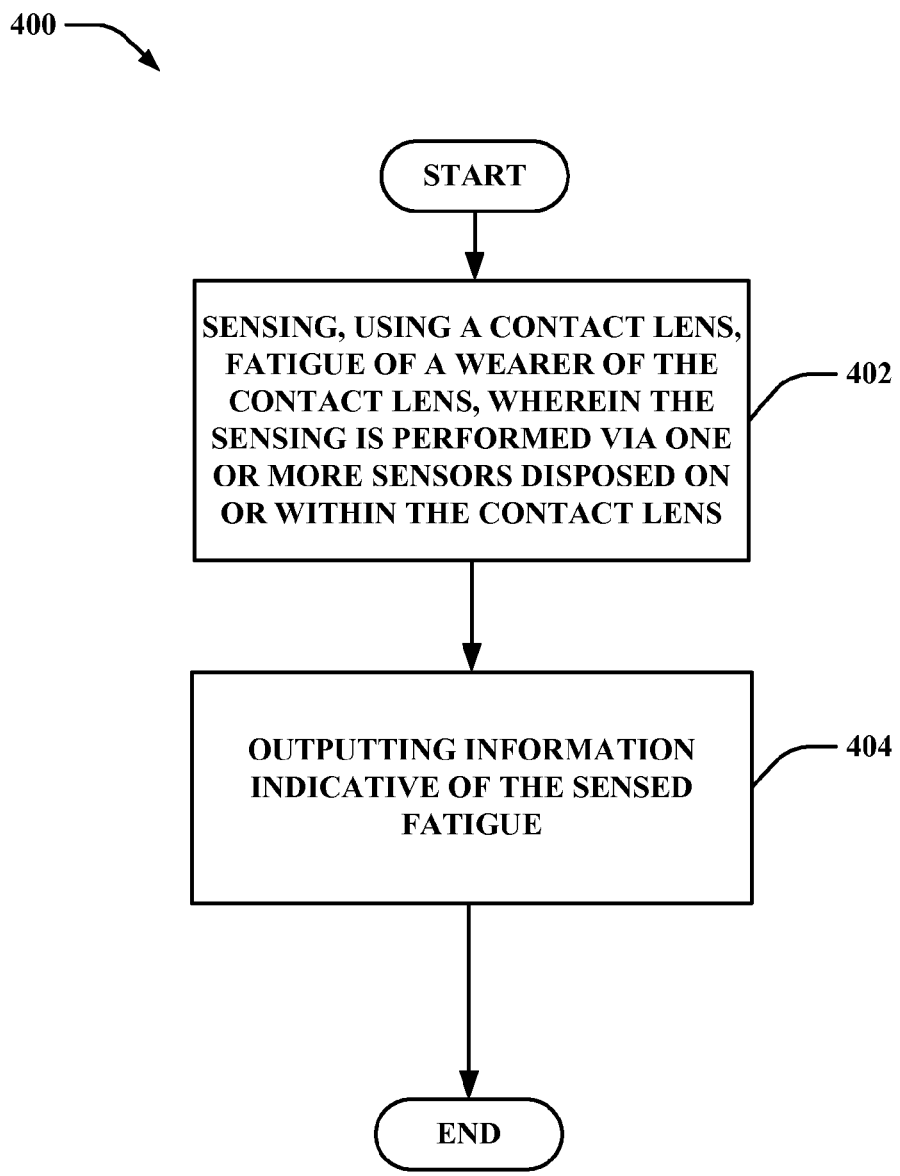
FIGS. 4, 5, 6, 7 and 8 are illustrations of exemplary flow diagrams of methods that facilitate detection of fatigue and/or emotional states of wearers of contact lenses.

FIGS. 4, 5, 6, 7 and 8 are illustrations of exemplary flow diagrams of methods that facilitate detection of fatigue and/or emotional states of wearers of contact lenses. Turning first to FIG. 4, at 402, method 400 can include sensing, using a contact lens, fatigue of a wearer of a contact lens (e.g., using one or more of the sensors 206, 208). As noted, in some aspects, the sensing is performed via one or more sensors disposed on or within the contact lens.

In various aspects, the fatigue can be sensed by sensing neural activity, electromyogram activity and/or a biomarker level of the wearer of the contact lens.

Although not shown, in some aspects, a method can include sensing the behavior of an eye over which the contact lens is disposed. The behavior can include a duration during which the eye is closed and/or a frequency of blinking of the eyelid. Such information can be employed to deduce fatigue in various aspects (e.g., if blink events are detected to be exceeding a threshold of 5 blinks per minute, for example, the system may deduce that the wearer is fatigued).

At 404, method 400 can include outputting information indicative of the sensed fatigue (e.g., using the communication component 212).

Figure 5:
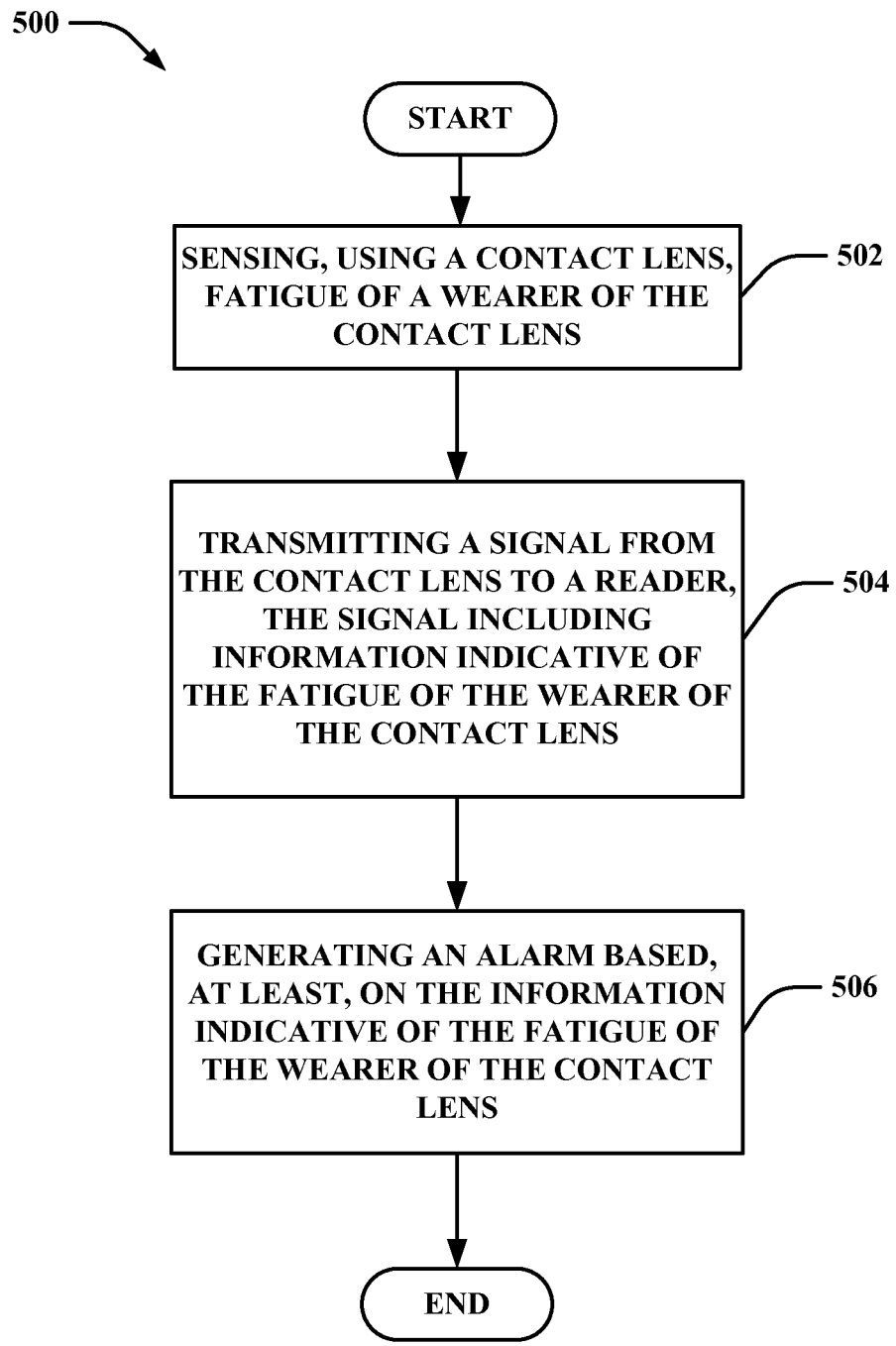

Turning now to FIG. 5, at 502, method 500 can include sensing, using a contact lens, fatigue of the wearer of the contact lens (e.g., using one or more of the sensors 206, 208). In various aspects, the fatigue can be sensed by sensing neural activity, electromyogram activity and/or a biomarker level of the wearer of the contact lens. For example, as described above, the sensors 206, 208 can detect the electrical activity from nerve cells in the eye muscles. The electromyogram activity can be the electrical activity from the nerve cells in the eye muscles. If the amount of electrical activity decreases by a predetermined amount over a particular time period, the contact lens 200 can determine that the wearer is fatigued. As another example, in various aspects, levels of adrenaline, epinephrine, and/or norepinephrine below a particular threshold can be detected and can be determined to indicate fatigue. As another example, a level of lactate or hydrogen ions above a particular threshold can be detected and can be determined to indicate fatigue. As another example, a level of fluid near the eye can indicate the level of puffiness of the eye. The level of fluid can be employed to determine whether the wearer is fatigued.

At 504, method 500 can include transmitting a signal from the contact lens to a reader (e.g., using the communication component 212). In various aspects, the signal can include information indicative of the fatigue of the wearer of the contact lens. The information indicative of the fatigue can include, but is not limited to, electrical activity from nerve cells in the eye muscles, a number of blinks of the eyelid over a period of time, and/or a level of adrenaline, epinephrine, norepinephrine, lactate and/or hydrogen ions in the fluid incident on the contact lens.

At 506, method 500 can include generating an alarm based, at least, on the information indicative of the fatigue of the wearer of the contact lens (e.g., using the alarm generation component 112).

Figure 6:
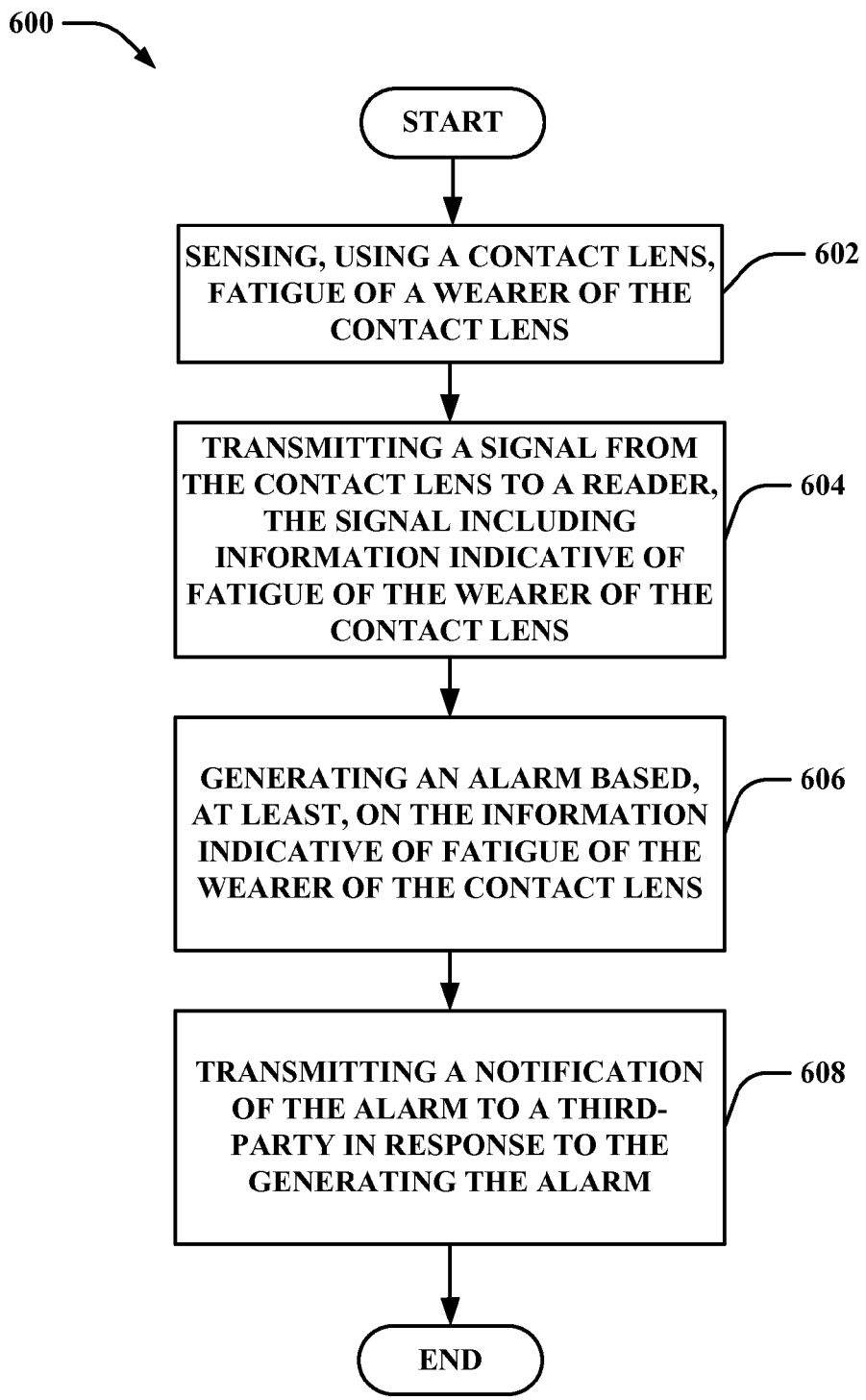

Turning now to FIG. 6, at 602, method 600 can include sensing, using a contact lens, fatigue of a wearer of the contact lens (e.g., using one or more of the sensors 206, 208). In various aspects, the fatigue can be sensed by sensing neural activity, electromyogram activity and/or a biomarker level of the wearer of the contact lens. For example, as described above, the sensors 206, 208 can detect the electrical activity from nerve cells in the eye muscles. The electromyogram activity can be the electrical activity from the nerve cells in the eye muscles. If the amount of electrical activity decreases by a predetermined amount over a particular time period, the contact lens 200 can determine that the wearer is fatigued. As another example, in various aspects, levels of adrenaline, epinephrine, and/or norepinephrine below a particular threshold can be detected and can be determined to indicate fatigue. As another example, a level of lactate or hydrogen ions above a particular threshold can be detected and can be determined to indicate fatigue. As another example, a level of fluid near the eye can indicate the level of puffiness of the eye. The level of fluid can be employed to determine whether the wearer is fatigued At 604, method 600 can include transmitting a signal from the contact lens to a reader (e.g., using the communication component 212). In various aspects, the signal can include information indicative of the fatigue of the wearer of the contact lens.

At 606, method 600 can include generating an alarm based, at least, on the information indicative of the fatigue of the wearer of the contact lens (e.g., using the alarm generation component 112).

At 608, method 600 can include transmitting a notification of the alarm to a third-party in response to the generating the alarm (e.g., using the alarm action component 114).

Figure 7:
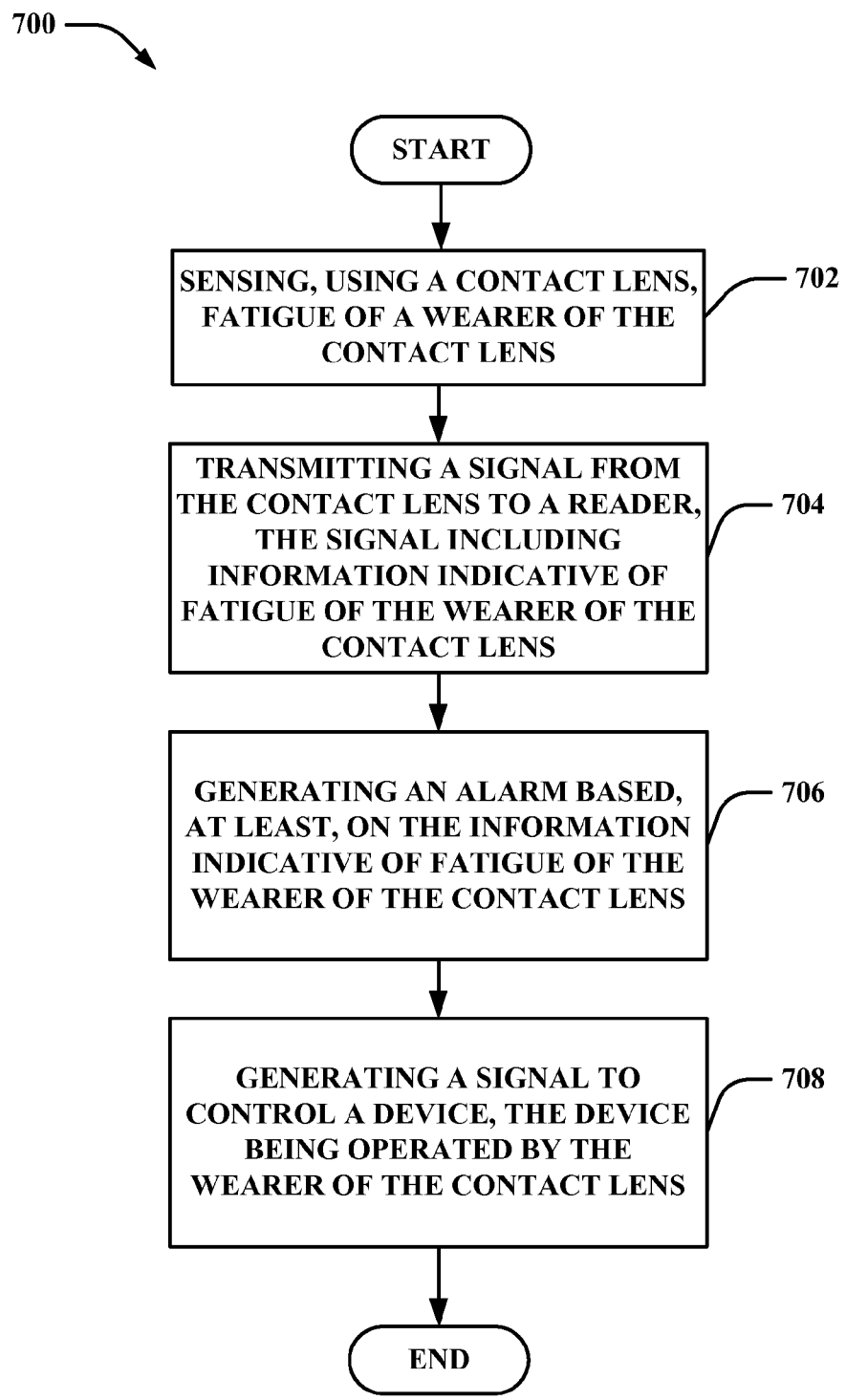

Turning now to FIG. 7, at 702, method 700 can include sensing, using a contact lens, fatigue of the wearer of the contact lens (e.g., using one or more of the sensors 206, 208). In various aspects, the fatigue can be sensed by sensing neural activity, electromyogram activity and/or a biomarker level of the wearer of the contact lens. For example, as described above, the sensors 206, 208 can detect the electrical activity from nerve cells in the eye muscles. The electromyogram activity can be the electrical activity from the nerve cells in the eye muscles. If the amount of electrical activity decreases by a predetermined amount over a particular time period, the contact lens 200 can determine that the wearer is fatigued. As another example, in various aspects, levels of adrenaline, epinephrine, and/or norepinephrine below a particular threshold can be detected and can be determined to indicate fatigue. As another example, level of lactate or hydrogen ions above a particular threshold can be detected and can be determined to indicate fatigue. As another example, a level of fluid near the eye can indicate the level of puffiness of the eye. The level of fluid can be employed to determine (or infer) whether the wearer is fatigued At 704, method 700 can include transmitting a signal from the contact lens to a reader (e.g., using the communication component 212). In various aspects, the signal can include information indicative of the fatigue of the wearer of the contact lens.

At 706, method 700 can include generating an alarm based, at least, on the information indicative of the fatigue of the wearer of the contact lens (e.g., using the alarm generation component 112).

At 708, method 700 can include generating a signal to control a device (e.g., using the alarm action component 114). In various aspects, the device can be operated by the wearer of the contact lens. The device can include, but is not limited to, a motorized vehicle, aircraft, machinery, electrically-powered surgical instrument or the like.

In some aspects, the signal can cause the device to cease operation and/or control the device to cause a more desirable condition to be effected. By way of example, but not limitation, in some aspects, the signal can cause the device to cease operation, fail to start operation and/or cease operation after a predetermined amount of time has passed after generation of the alarm and/or notification of the alarm. For example, the signal can be communicated to a base station or third-party that can transmit a wireless signal (from the BS or a satellite communicatively coupled to the device) causing the device to cease operation.

In some aspects, although not shown, the information from the sensor can be recorded in a data logging component. As such, information and/or trends of alarm times or the like can be recorded and/or provided to a wearer of the contact lens. Accordingly, the wearer can be informed as to particular times or days that have a higher frequency of fatigue and/or emotional state leading to an alarm.

Figure 8:
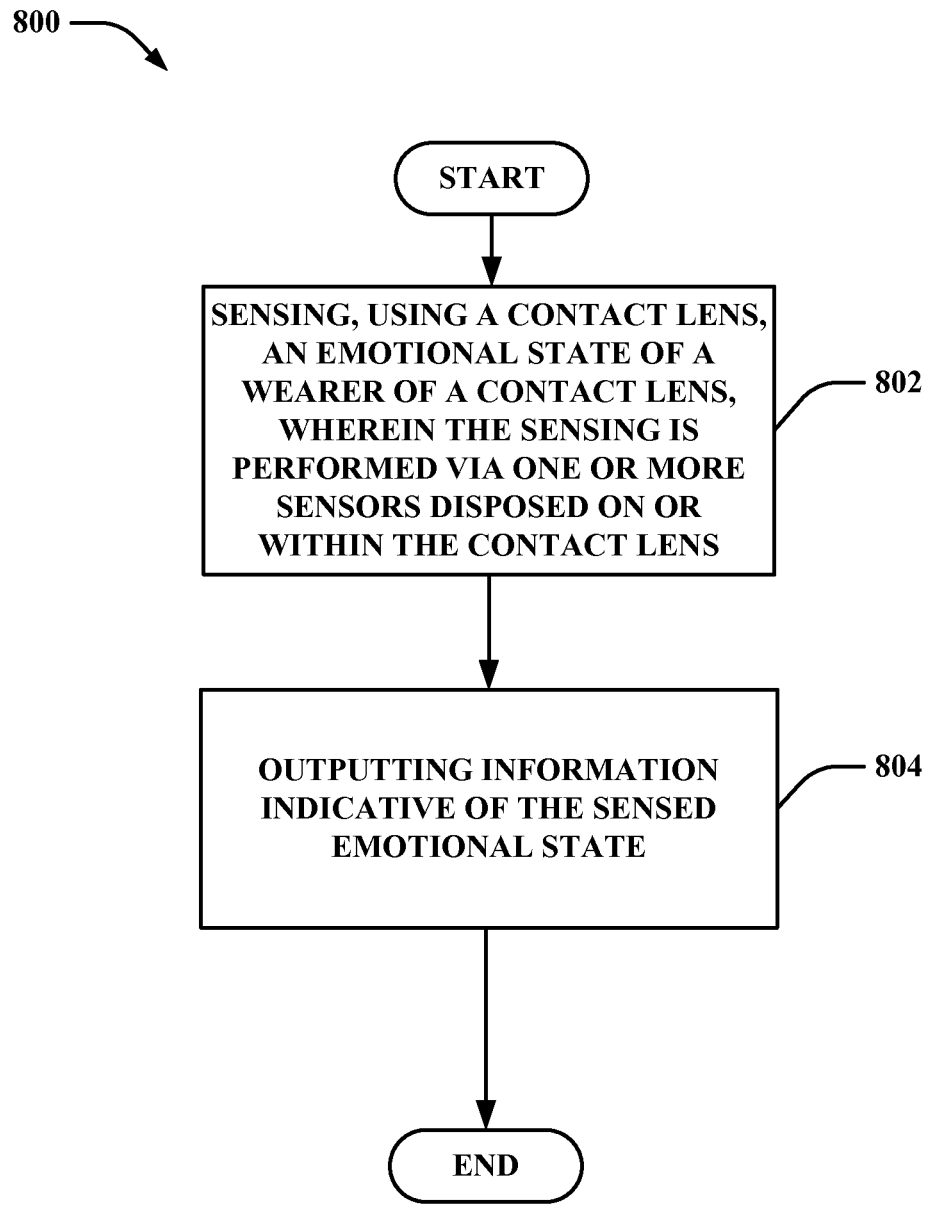

Turning now to FIG. 8, at 802, method 800 can include sensing, using a contact lens, an emotional state of a wearer of a contact lens (e.g., using one or more of the sensors 206, 208). In various aspects, the sensing can be performed via one or more of the sensors disposed on or within the contact lens.

In some aspects, the emotional state of the wearer of the contact lens can be sensed in addition to or in lieu of the fatigue. In various aspects, the emotional state can include, but is not limited to, whether the wearer is happy or sad. For example, in some aspects, a level of one or more chemicals (e.g., endorphins, serotonin) can be sensed in the body of the wearer of the contact lens. If the level is greater than a predetermined value, the emotional state of the wearer can be determined to be happy. Similarly, if the level is less than a value the emotional state of the wearer can be determined to be sad.

At 804, method 800 can include outputting information indicative of the sensed emotional state (e.g., using the communication component 212).

Exemplary Networked and Distributed Environments

Figure 9:
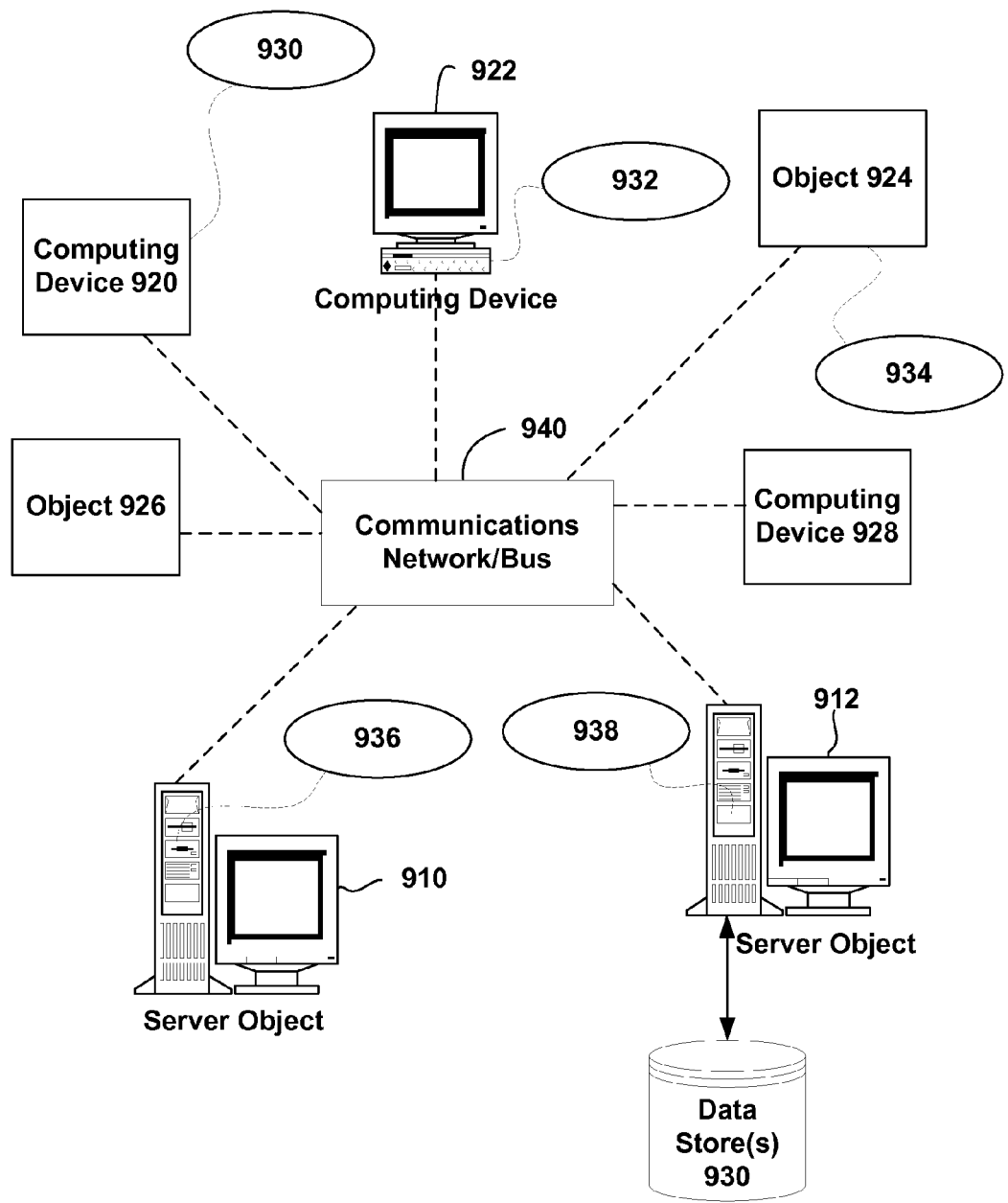
FIG. 9 is an illustration of a schematic diagram of an exemplary networked or distributed computing environment for implementing one or more aspects described herein.

FIG. 9 provides a schematic diagram of an exemplary networked or distributed computing environment with which one or more aspects described in this disclosure can be associated. The distributed computing environment includes computing objects 910, 912, etc. and computing objects or devices 920, 922, 924, 926, 928, etc., which can include programs, methods, data stores, programmable logic, etc., as represented by applications 930, 932, 934, 936, 938. It can be appreciated that computing objects 910, 912, etc. and computing objects or devices 920, 922, 924, 926, 928, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 910, 912, etc. and computing objects or devices 920, 922, 924, 926, 928, etc. can communicate with one or more other computing objects 910, 912, etc. and computing objects or devices 920, 922, 924, 926, 928, etc. by way of the communications network 940, either directly or indirectly. Even though illustrated as a single element in FIG. 9, network 940 can include other computing objects and computing devices that provide services to the system of FIG. 9, and/or can represent multiple interconnected networks, which are not shown.

In a network environment in which the communications network/bus 940 can be the Internet, the computing objects 910, 912, etc. can be Web servers, file servers, media servers, etc. with which the client computing objects or devices 920,

922, 924, 926, 928, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or reader described herein. In various aspects, the data store can include or be included within, any of the memory described herein, any of the contact lenses described herein and/or the RF reader described herein. In various aspects, the data store can be any repository for storing information transmitted to or received from the contact lens.

Figure 10:
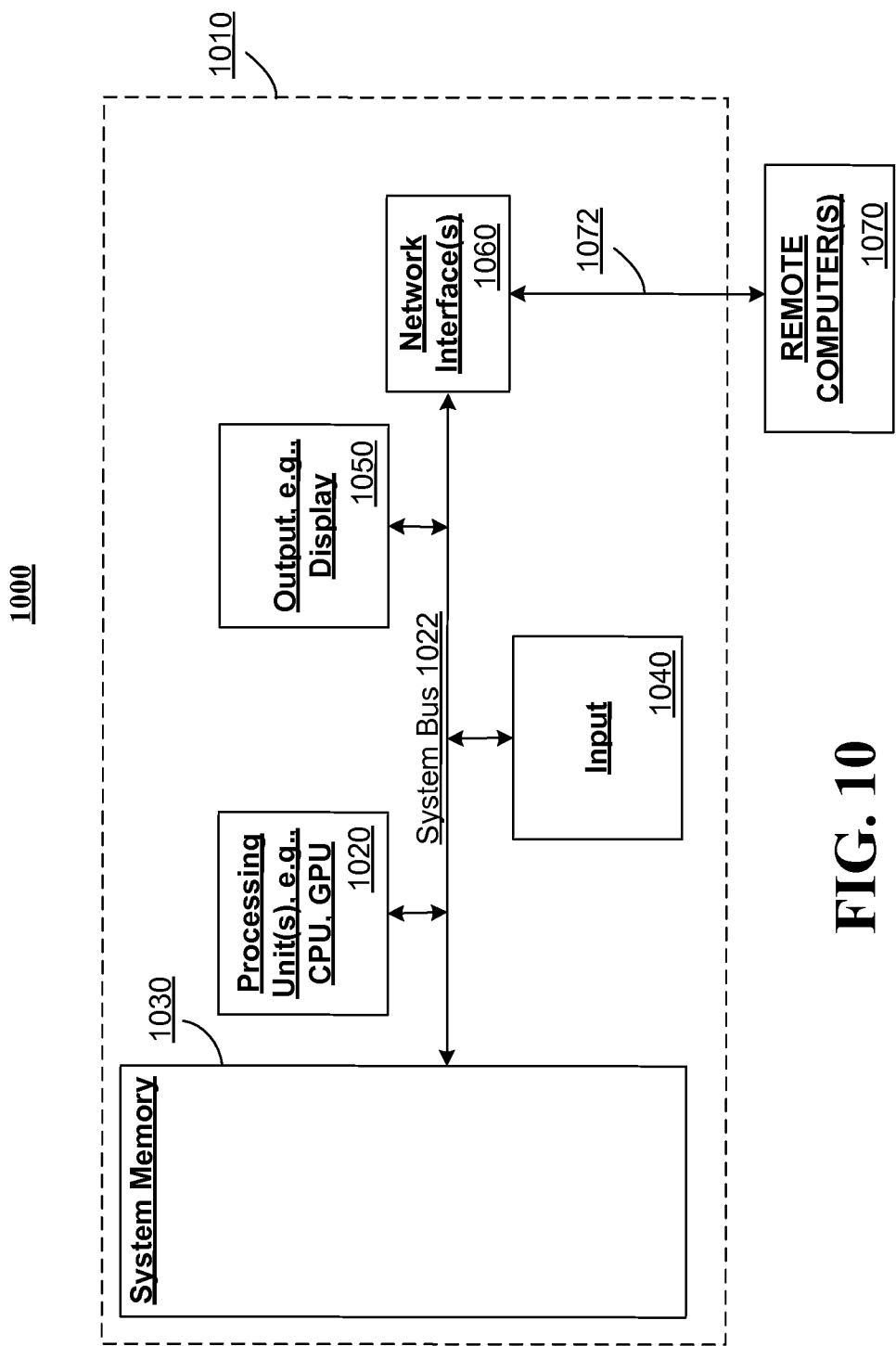
FIG. 10 is an illustration of a schematic diagram of an exemplary computing environment for implementing one or more aspects described herein.

FIG. 10 illustrates an example of a suitable computing system environment 1000 in which one or aspects of the aspects described in this disclosure can be implemented. Components of computer 1010 can include, but are not limited to, a processing unit 1020, a system memory 1030, and a system bus 1022 that couples various system components including the system memory to the processing unit 1020.

Computer 1010 typically includes a variety of computer readable media and can be any available media that can be accessed by computer 1010. The system memory 1030 can include computer storage media in the form of volatile and/or nonvolatile memory such as read only memory (ROM) and/or random access memory (RAM). By way of example, and not limitation, memory 1030 can also include an operating system, application programs, other program components, and program data.

A user can enter commands and information into the computer 1010 through input devices 1040 (e.g., keyboard, keypad, a pointing device, a mouse, stylus, touchpad, touch screen, motion detector, camera, microphone or any other device that allows the user to interact with the computer 1010). A monitor or other type of display device can be also connected to the system bus 1022 via an interface, such as output interface 1050. In addition to a monitor, computers can also include other peripheral output devices such as speakers and a printer, which can be connected through output interface 1050.

The computer 1010 can operate in a networked or distributed environment using logical connections to one or more other remote computers, such as remote computer 1080. The remote computer 1080 can be a personal computer, a server, a router, a network PC, a peer device or other common network node, or any other remote media consumption or transmission device, and can include any or all of the elements described above relative to the computer 1010. The logical connections depicted in FIG. 10 include a network 1082, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and nonvolatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
    a substrate; and
    a circuit comprising:
        one or more sensors, disposed on or within the substrate, wherein the one or more sensors include at least one light sensor configured to sense at least one of a duration of closure of an eyelid or a frequency of blinking; and
        an antenna disposed on or within the substrate, configured to communicate information sensed by the one or more sensors to a reader, wherein the information sensed by the one or more sensors is indicative of fatigue of a wearer of the contact lens based on calibration data, wherein the reader is configured to send a signal to at least one component based on the information indicative of fatigue of the wearer of the contact lens.

2. The contact lens of claim 1, wherein the information sensed by the one or more sensors is further indicative of an emotional state of the wearer of the contact lens.

3. The contact lens of claim 1, wherein the one or more sensors further include at least one sensor configured to sense at least one of neural activity or electromyogram activity of the wearer of the contact lens.

4. The contact lens of claim 1, wherein the one or more sensors further include at least one sensor configured to sense a level of fluid retention around an eye over which the contact lens is disposed.

5. The contact lens of claim 1, wherein the one or more sensors further include at least one sensor configured to sense a level of at least one of lactate, hydrogen ions, adrenaline, serotonin, dopamine, epinephrine or norepinephrine.

6. The contact lens of claim 1, wherein the calibration data comprises a baseline corresponding to a non-fatigued state of the wearer of the contact lens, such that a variance from the baseline is indicative of a fatigued state of the wearer of the contact lens.

7. The contact lens of claim 1, wherein the at least one component comprises a component configured to generate an alarm based on the signal from the reader.

8. The contact lens of claim 1, wherein the at least one component comprises a component configure to control a device operated by the wearer of the contact lens based on the signal from the reader.

9. The contact lens of claim 1, wherein the at least one component comprises a data logging component.

10. The contact lens of claim 1, wherein the reader is configured to compare the information sensed by the one or more sensors to one more thresholds.

11. A method, comprising:
    sensing, using a contact lens, fatigue of a wearer of the contact lens, wherein the sensing is performed via one or more sensors disposed on or within the contact lens, wherein the one or more sensors include at least one light sensor configured to sense at least one of a duration of closure of an eyelid or a frequency of blinking; and
    communicating information sensed by the one or more sensors to a reader, wherein the information sensed by the one or more sensors is indicative of fatigue of the wearer of the contact lens based on calibration data, wherein the reader is configured to send a signal to at least one component based on the information indicative of fatigue of the wearer of the contact lens.

12. The method of claim 11, further comprising sensing an emotional state of the wearer of the contact lens.

13. The method of claim 12, wherein the sensing the emotional state comprises sensing a level of at least one of dopamine or serotonin.

14. The method of claim 11, wherein the sensing the fatigue comprises sensing at least one of neural activity or electromyogram activity of the wearer of the contact lens.

15. The method of claim 11, wherein the one or more sensors further include at least one sensor configured to sense a level of fluid near an eye over which the contact lens is disposed.

16. The method of claim 11, wherein the calibration data comprises a baseline corresponding to a non-fatigued state of the wearer of the contact lens, such that a variance from the baseline is indicative of a fatigued state of the wearer of the contact lens.

17. The method of claim 11, wherein the at least one component comprises a component configured to generate an alarm based on the signal from the reader.

18. The method of claim 11, wherein the at least one component comprises a component configure to control a device operated by the wearer of the contact lens based on the signal from the reader.

19. The method of claim 11, wherein the at least one component comprises a data logging component.

20. The method of claim 11, wherein the reader is configured to compare the information sensed by the one or more sensors to one more thresholds.

* * * * *